(12) United States Patent
Kim et al.

(10) Patent No.: US 9,084,739 B2
(45) Date of Patent: Jul. 21, 2015

(54) CROSS-LINKED COPOLYMER CONTAINING PHOSPHORYLCHOLINE MONOMER AND COSMETIC COMPOSITION CONTAINING SAME

(75) Inventors: Yong Chul Kim, Gunpo-si (KR); Hyeong Bae Kim, Seoul (KR); In Sun Han, Seoul (KR); Se Kwan Wang, Bucheon-si (KR); Jung Ho Park, Yongin-si (KR)

(73) Assignee: KCI Limited, Seonsan-si (KR)

( * ) Notice: Subject to any disclaimer, the term of this patent is extended or adjusted under 35 U.S.C. 154(b) by 22 days.

(21) Appl. No.: 13/978,625

(22) PCT Filed: Nov. 23, 2011

(86) PCT No.: PCT/KR2011/008989
§ 371 (c)(1),
(2), (4) Date: Jul. 8, 2013

(87) PCT Pub. No.: WO2012/093774
PCT Pub. Date: Jul. 12, 2012

(65) Prior Publication Data
US 2013/0295038 A1    Nov. 7, 2013

(30) Foreign Application Priority Data

Jan. 7, 2011 (KR) .................. 10-2011-0001978
Nov. 23, 2011 (KR) .................. 10-2011-0122960

(51) Int. Cl.
*A61K 8/02* (2006.01)
*A01N 25/28* (2006.01)
*A61K 8/81* (2006.01)
*A61Q 5/12* (2006.01)
*A61Q 19/00* (2006.01)
*C08F 220/06* (2006.01)

(52) U.S. Cl.
CPC ............. *A61K 8/8147* (2013.01); *A61K 8/8152* (2013.01); *A61Q 5/12* (2013.01); *A61Q 19/00* (2013.01); *C08F 220/06* (2013.01)

(58) Field of Classification Search
None
See application file for complete search history.

(56) References Cited

U.S. PATENT DOCUMENTS 6,858,673 B1    2/2005    Sakamoto et al.
2010/0249273 A1    9/2010    Scales et al.

FOREIGN PATENT DOCUMENTS

JP    6157270 A    6/1994
KR    100977621 B1    8/2010

OTHER PUBLICATIONS

Kiritoshi et al., Preparation of cross-linked biocompatible poly (2-methacryloyloxyethyl phosphorylcholine) gel and its strange swelling behavior in water/ethanol mixture, J. Biomater. Sci. Polymer Edn, 2002, pp. 213-224, vol. 13, No. 2.

*Primary Examiner* — Susan Tran
(74) *Attorney, Agent, or Firm* — The Webb Law Firm

(57) ABSTRACT

Disclosed is a copolymer containing an $\alpha,\beta$-ethylenically unsaturated monomer, a phosphorylcholine monomer, and a cross-linking agent as a monomer. Also disclosed are a cosmetic composition containing the copolymer and a cosmetic material using the cosmetic composition.

8 Claims, No Drawings

CROSS-LINKED COPOLYMER CONTAINING PHOSPHORYLCHOLINE MONOMER AND COSMETIC COMPOSITION CONTAINING SAME

CROSS-REFERENCE TO RELATED APPLICATIONS

This application is the United States national phase under 35 U.S.C. §371 of International Application No. PCT/KR2011/008989 filed Nov. 23, 2011, entitled "Cross-Linked Copolymer Containing Phosphorylcholine Monomer and Cosmetic Composition Containing Same", and claims priority under 35 U.S.C. §119(a)-(d) to Korean Patent Application Nos. 10-2011-0001978, filed on Jan. 7, 2011, and 10-2011-0122960 filed on Nov. 23, 2011 in the Korean Intellectual Property Office, the disclosures of which are hereby incorporated by reference in their entirety.

TECHNICAL FIELD

The present invention relates to a cross-linked copolymer containing a phosphorylcholine monomer, a cosmetic composition containing the same, and a cosmetic material containing the cosmetic composition.

In more detail, the present invention relates to a cross-linked copolymer prepared using α,β-ethylenically unsaturated monomer, a phosphorylcholine monomer having a specific structure containing a phosphorylcholine unit, and a cross-linking agent, a cosmetic composition containing the cross-linked copolymer, and a cosmetic material prepared using the composition.

BACKGROUND ART

A polymer containing acrylic acid or methacrylic acid has been used for various uses such as a thickener, a dispersant, an emulsifier, a super-absorbent polymer, and the like, in a pharmaceutical or cosmetic field. However, it was known that the acrylic acid or methacrylic acid based polymer has excellent water absorbing and holding capacity and may be expanded by several ten times as compared to its original volume, but there are disadvantages in that the polymer irritates skin and does not have or insufficiently has a function of sufficiently protecting the skin at the time of using the polymer for a long period of time.

Therefore, an object of the present invention is to provide a material capable of being widely used in the cosmetic field, a cosmetic composition containing the material, and a cosmetic material containing the composition by preparing a polymer having the advantages of the (meth)acrylic acid base polymer, a function of alleviating skin irritation or protecting the skin, and a new structure.

DISCLOSURE

Technical Problem

An object of the present invention is to provide a new copolymer capable of overcoming disadvantages according to the related art and having significantly excellent properties in view of a thickening property, emulsion stability, an absorption property, or dispersibility.

Another object of the present invention is to provide a new copolymer having properties such as excellent biocompatibility, an improved moisturizing effect, a skin barrier function improving property, and the like, in addition to the existing thickening function.

Further, another object of the present invention is to provide a composition containing the polymer having the new properties, and a cosmetic material using the composition.

Technical Solution

In one general aspect, a cross-linked copolymer contains: at least one kind of α,β-ethylenically unsaturated monomers; a phosphorylcholine monomer containing a phosphorylcholine unit of Chemical Formula (1); and at least one kind of cross-linking agent having at least two unsaturated ethylene bonding groups capable of being cross-linked with the phosphorylcholine monomer and the α,β-ethylenically unsaturated monomer as a monomer. Particularly, in the present invention, it may be appreciated that the cross-linked copolymer may have significantly excellent effects as compared to the existing materials known in the art such as polyacrylic acid, and the like, and be universally applied to various technical fields by preparing the copolymer cross-linked using the cross-linking agent while containing the monomer of the present invention.

Hereinafter, constituent monomer components of the present invention and a method of preparing a polymer thereof will be described.

The cross-linked copolymer based on the phosphorylcholine monomer is characterized in that a content of the phosphorylcholine monomer in the cross-linked copolymer (hereinafter, referred to as the 'copolymer') may be 0.1 to 80 parts by weight, and a content of the cross-linking agent may be 0.01 to 30 parts by weight, based on 100 parts by weight of the α,β-ethylenically unsaturated monomer.

[Chemical Formula 1]

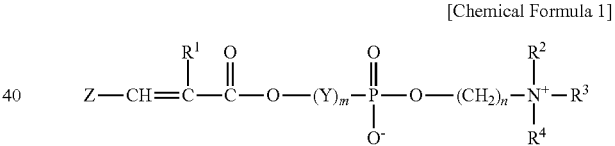

In Chemical Formula (1), Z is a hydrogen atom or $R^5$—O—CO— (here, $R^5$ is a hydrogen atom, an alkyl group having 1 to 10 carbon atoms, or a hydroxyalkyl group having 1 to 10 carbon atoms), and Y is an alkyleneoxy group having 1 to 20 carbon atoms. In addition, $R^1$ is a hydrogen atom or a hydrocarbon group having 1 to 5 carbon atoms, and $R^2$, $R^3$ and $R^4$ are a hydrogen atom or a hydrocarbon or hydroxy hydrocarbon group having 1 to 6 carbon atoms as the same group or different groups. Further, m is an integer of 1 to 20, and n is an integer of 2 to 5.

In the copolymer according to the present invention, a kind of α,β-ethylenically unsaturated monomer is not particularly limited but may be preferably acrylic acid or methacrylic acid in view of a thickening property, emulsion stability, an absorption property, and the like. Further, a kind of phosphorylcholine monomer also is not particularly limited but may be preferably 2-(methacryloyloxy)ethyl-2'-(trimethylammonio)ethylphosphate in view of a moisturizing property and biocompatibility. In addition, a 0.5 weight % aqueous solution of the copolymer prepared as described may have a neutral viscosity (viscosity at pH 7.0) of 1,000 to 500,000 centipoises (cps).

In another general aspect, a cosmetic composition contains the copolymer as an active ingredient. The cosmetic composition according to the present invention may be used for skin care or hair care, and a content of the copolymer in the composition is not particularly limited but may be preferably 0.01 to 10 weight % based on the total weight of the composition in view of a thickening effect, an emulsion stability, a dispersion property, a moisturizing property, and the like.

Advantageous Effects

A copolymer according to the present invention, which is a copolymer containing a cross-linking agent, and an α,β-ethylenically unsaturated monomer and a phosphorylcholine monomer as a monomer, may have excellent properties in view of improving a thickening effect, emulsion stability, a dispersion property, or the like, as compared to other polymers developed according to the related art, for example, an acrylic acid based polymer. Particularly, the copolymer may have unexpected excellent effects in view of an improved moisturizing effect, skin barrier function improvement and excellent biocompatibility. In addition, a cosmetic composition containing the copolymer according to the present invention may have a skin moisturizing effect, an atopic dermatitis alleviating effect, an inflammation alleviating effect, spreadability, a hair conditioning effect to thereby be variously used for skin care or hair care.

BEST MODE

In one general aspect, as described above, the present invention relates to a new cross-linked copolymer imparting a thickening effect, emulsion stability, a moisturizing effect, a skin barrier function improving effect and biocompatibility to a cosmetic composition. The copolymer according to the present invention contains a phosphorylcholine monomer, an α,β-ethylenically unsaturated monomer and a cross-linking agent.

Hereinafter, a new polymer according to the present invention will be described.

α,β-Ethylenically Unsaturated Monomer

The copolymer according to the present invention is prepared using one or at least two α,β-ethylenically unsaturated monomers as a monomer. The α,β-ethylenically unsaturated monomer may preferably include α,β-ethylenically unsaturated carboxylic acid. As the α,β-ethylenically unsaturated carboxylic acid, there are monobasic acid such as acrylic acid, methacrylic acid, crotonic acid, acyloxypropenoic acid, or the like, dibasic acid such as maleic acid, fumaric acid, itaconic acid and the like, and each of them may be used alone, or a mixture thereof may be used.

In the present invention, a material obtained by mixing a monomer having a structure of the following Chemical Formula (2) with an α,β-ethylenically unsaturated monomer may be considered as an α,β-ethylenically unsaturated monomer.

A content of the monomer of the following Chemical Formula (2) may be 40 to 99.9%, preferably 55 to 99.9%, based on 100 parts by weight of the α,β-ethylenically unsaturated monomer.

Chemical Formula (2)

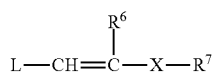

Where, L is a hydrogen atom or $R^8$—O—CO—, $R^8$ is a hydrogen atom, an alkyl group having 1 to 10 carbon atoms, or an hydroxyalkyl group having 1 to 10 carbon atoms, X is any one selected from

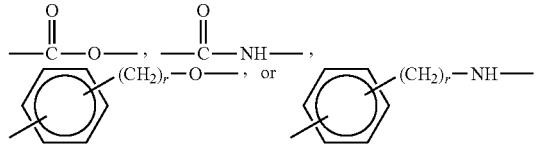

and r is an integer of 1 to 10. In addition, $R^6$ is a hydrogen atom, an alkyl group having 1 to 5 carbon atoms, a halogen atom, a hydroxy group, or a cyano group and $R^7$ is a hydrogen atom or a hydrocarbon group having 1 to 30 carbon atoms.

A specific example of the monomer represented by Chemical Formula (2) may include methyl acrylate, ethyl acrylate, propyl acrylate, isopropyl acrylate, butyl acrylate, isobutyl acrylate, octyl acrylate, heptyl acrylate, decyl acrylate, isodecyl acrylate, lauryl acrylate, stearyl acrylate, behenyl acrylate and melissyl acrylate, methacrylates corresponding thereto, and the like, and at least one kind thereof may be selected and used as the monomer.

Phosphorylcholine Monomer

The present invention includes a phosphorylcholine monomer having a structure of the following Chemical Formula (1).

Chemical Formula (1)

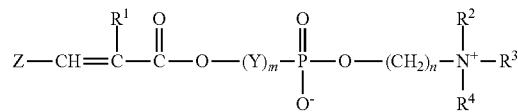

In Chemical Formula (1), Z is a hydrogen atom or $R^5$—O—CO—, $R^5$ is a hydrogen atom, an alkyl group having 1 to 10 carbon atoms, or a hydroxyalkyl group having 1 to 10 carbon atoms, and Y is an alkyleneoxy group having 1 to 20 carbon atoms. In addition, $R^4$ is a hydrogen atom or a hydrocarbon group having 1 to 5 carbon atoms, and $R^2$, $R^3$ and $R^4$ are a hydrogen atom, a hydrocarbon or hydroxy hydrocarbon group having 1 to 6 carbon atoms as the same group or different groups. Further, m is an integer of 1 to 20, and n is an integer of 2 to 5.

As an example of the phosphorylcholine monomer represented by Chemical Formula (1), there are 2-((meth)acryloyloxy)ethyl-2'-(trimethylammonio)ethylphosphate, 3-((meth)acryloyloxy)propyl-2'-(trimethylammonio)ethylphosphate, 4-((meth)acryloyloxy)butyl-2'-(trimethylammonio)ethylphosphate, 5-((meth)acryloyloxy)pentyl-2'-(trimethylammonio)ethylphosphate, 6-((meth)acryloyloxy)hexyl-2'-(trimethylammonio)ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethylphosphate, 2-((meth)acryloyloxy)propyl-2'-(trimethylammonio)ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethylphosphate, ethyl-(2'-trimethylammonio ethylphosphorylethyl)fumarate, butyl-(2'-trimethylammonio ethylphosphorylethyl)fumarate, hydroxyethyl-(2'-trimethylammonio ethylphosphorylethyl)

fumarate, ethyl-(2'-trimethylammonio ethylphosphorylethyl)fumarate, butyl-(2'-trimethylammonio ethylphosphorylethyl)fumarate, hydroxyethyl-(2'-trimethylammonio ethylphosphorylethyl)fumarate, and the like, and one of them may be used alone, or a mixture thereof may be used. In the phosphorylcholine monomer, the term "((meth)acryloyloxy) ethyl", etc, means both of acryloyloxyethyl and methacryloyloxyethyl, etc.

The phosphorylcholine monomer according to the present invention is not particularly limited but may be preferably 2-(methacryloyloxy)ethyl-2'-(trimethylammonio)ethylphosphate (which is also called 2-methacryloyloxyethylphosphorylcholine, hereinafter, called MPC for short) in view of the absorption property and biocompatibility.

A content of the phosphorylcholine monomer in the copolymer according to the present invention may be 0.1 to 80 parts by weight, preferably 0.5 to 10 parts by weight, based on 100 parts by weight of the α,β-ethylenically unsaturated monomer. In the case in which the content of the phosphorylcholine monomer in the copolymer is lower than 0.1 parts by weight, based on 100 parts by weight of the α,β-ethylenically unsaturated monomer, the moisturizing property and biocompatibility of the copolymer may be incomplete, and in the case in which the content of a material containing a phosphorylcholine-like group in the copolymer is higher than 80 parts by weight, based on 100 parts by weight of the α,β-ethylenically unsaturated monomer, the thickening effect of the copolymer may not be increased any more.

Cross-Linking Agent

The cross-linking agent according to the present invention includes at least one kind of cross-linking agent having at least two unsaturated ethylene bonding groups. In the present invention, the cross-linking agent may cross-link the phosphorylcholine monomer and the α,β-ethylenically unsaturated monomer to each other to form a network structure and allow the copolymer according to the present invention to have a stable thickening effect in a wide range of pH and in a presence of a salt.

A kind of cross-linking agent of the copolymer according to the present invention is not particularly limited as long as it may bind to the phosphorylcholine monomer and the α,β-ethylenically unsaturated monomer by a radical polymerization reaction. For example, as the cross-linking agent, ethylene glycol diacrylate, ethylene glycol dimethacrylate, propylene glycol diacrylate, propylene glycol dimethacrylate, butylene glycol diacrylate, butylene glycol dimethacrylate, hexylene glycol diacrylate, hexylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, allyl acrylate, allyl methacrylate, methallyl acrylate, allyl ethacrylate, ethallyl acrylate, methallyl methacrylate, diallyl phthalate, diallyl maleate, diallyl succinate, triallyl phosphate, diallyl oxalate, diallyl malonate, diallyl citrate, diallyl fumarate, divinyl benzene, trivinyl benzene, vinyl crotonate, N,N-methylene-bis-acrylamide, trimethylolpropane diallyl ether, trimethylolpropane triallyl ether, diallyl pentaerythritol ether, triallyl pentaerythritol ether, tetraallyl pentaerythritol ether, diallyl sucrose ether, triallyl sucrose ether, tetraallyl sucrose ether, pentaallyl sucrose ether, hexaallyl sucrose ether, or the like, may be used alone, or a mixture thereof may be used.

A content of the cross-linking agent according to the present invention may be 0.01 to 30 parts by weight, preferably 0.05 to 10 parts by weight, and more preferably 0.1 to 5 parts by weight, based on 100 parts by weight of the α,β-ethylenically unsaturated monomer. In the case in which the content of the cross-linking agent is lower than 0.01 parts by weight, based on 100 parts by weight of the α,β-ethylenically unsaturated monomer, the thickening effect of the copolymer may be incomplete, and in the case in which the content of the cross-linking agent is higher than 30 parts by weight, based on 100 parts by weight of the α,β-ethylenically unsaturated monomer, some of the copolymers may not swell in water, such that effects of the copolymer may be deteriorated.

Hereinafter, a method of preparing a copolymer according to the present invention will be described.

The copolymer according to the present invention may be prepared by a method such as a suspension polymerization method, a reverse-emulsion polymerization method, and a precipitation polymerization method that use an organic solvent as a reactive medium, a solution method using water as a reactive medium, or the like, and generally, in these polymerization methods, a radical polymerization reaction is used. Hereinafter, as an example of the present invention, the precipitation polymerization method will be described.

First, an organic solvent, the α,β-ethylenically unsaturated monomer, and the phosphorylcholine monomer are put into a reactor and dissolved, followed by purging the reactor with inert gas. Then, the reactor is purged with the inert gas again while raising a temperature to about 50-90° C. Thereafter, the cross-linking agent and a polymerization initiator are dissolved in the organic solvent and added to a reactor heated to about 5090° C., followed by performing a polymerization reaction for about 3 to 10 hours. When the polymerization reaction is terminated, the copolymer is precipitated. In this case, after filtration, the organic solvent is removed through vacuum evaporation at about 70-110° C., thereby making it possible to obtain a white powder type copolymer.

Here, preferably, the copolymer may be prepared under inert gas atmosphere such as nitrogen, carbon dioxide, helium, or the like. The organic solvent is not particularly limited, but may be preferably an organic solvent capable of dissolving the α,β-ethylenically unsaturated monomer and the phosphorylcholine monomer, and more preferably an organic solvent capable of dissolving also the cross-linking agent. An example of the organic solvent may include toluene, benzene, cyclohexane, ethylacetate, cyclohexane and ethylacetate, n-hexane, methyl ethyl ketone, and the like. Among them, any one may be selected to be used, or at least one organic solvent may be suitably mixed to be used. For example, a mixed solvent in which the organic solvent is mixed at a weight ratio of 1:99 to 99:1 may be used.

At the time of performing the radical reaction in the organic solvent, propagation of a chain having a predetermine length or more may occur, and if the grown polymer is not dissolved in the organic solvent and precipitated therein according to the polarity value of the used organic solvent, the polymerization reaction is terminated. The length of the polymer chain as described above may be adjusted according to the mixing ratio of the mixed solvent. Further, in the case of using water as the solvent, the copolymer may be prepared by an emulsion polymerization method.

An example of the radical polymerization initiator according to the present invention may include an azo initiator such as azobisisobutyronitrile (AIBN), azobisdimethylvaleronitrile, peroxycarbonate such as benzoyl peroxide, lauroyl peroxide, potassium persulfate, di(2-ethylhexyl)peroxydicarbonate, di(sec-butyl)peroxydicarbonate, di(isopropyl) peroxydicarbonate, di(cyclohexyl)peroxydicarbonate, di(cetyl)peroxydicarbonate, di(n-propyl)peroxydicarbonate, and the like. As a commercial product of the polymerization initiator, there are Vazo 52, Vazo 64, Vazo 67 and Vazo 88 produced by Dupont, and the like. The initiator is selected in consideration of a half lift time of the initiator at each temperature and a boiling point of the organic solvent. A 0.5 weight % aqueous solution of the copolymer prepared by the above-mentioned method may have a viscosity of 1,000 to 500,000 centipoises (cps) at pH 7.0.

Cosmetic Composition

In another general aspect, the present invention relates to a cosmetic composition containing the above-mentioned copolymer as an active ingredient. In the present invention, the cosmetic composition, which is a material used in the body in order to clean and beautify the body to thereby make a face attractive and bright or in order to maintain or improve health of skin or hair, is a wide concept including personal hygiene care products such as detergents and bath agents.

The copolymer according to the present invention is added to the cosmetic composition as one ingredient to serve as a thickening agent, an emulsion stabilizer and a moisturizing agent and impart excellent biocompatibility to the cosmetic composition. In detail, the cosmetic composition containing the copolymer according to the present invention as the active ingredient may be used for skin care or hair care. In the case in which the cosmetic composition is used for skin care, the cosmetic composition may improve skin absorption and skin barrier functions, and in the case in which the cosmetic composition is used for hair care, the cosmetic composition may improve dissolubility and protect damaged hair, and the like. A content of the copolymer in the cosmetic composition may be various according to the use and formulation of the cosmetic composition but may be preferably 0.01 to 10 weight % based on the total weight of the composition in view of feeling after use (for example, spreadability), moisturization, and the like.

The cosmetic composition according to the present invention may contain various ingredients, for example, a preserving agent, an osmotic agent, a pH adjusting agent, a buffering agent, a stabilizer, aluminum hydroxide, aluminum phosphate, a surfactant, liposome, a thickening agent, or the like, ingredients generally used in cosmetic compositions, for example, general aids such as an antioxidant, a dissolving agent, a vitamin, a pigment and a fragrance, a carrier, and the like, in addition to an aqueous medium and the copolymer, but is not limited thereto. According to a preferable embodiment of the present invention, the content of the copolymer is 0.001 to 30 weight %, preferably 0.01 to 10 weight % based on the total weight of the cosmetic composition. In preferable Examples of the present invention, a cosmetic composition containing 0.5 weight % of the copolymer according to the present invention was prepared, and it was confirmed that the composition had excellent skin moisturizing and atopic dermatitis alleviating effects by directly applying the composition onto skin.

The cosmetic composition according to the present invention may be used in any formulation generally prepared in the art. For example, the cosmetic composition may be formulated as a solution, a suspension, an emulsion, a paste, a gel, a cream, a lotion, powder, soap, surfactant-containing cleansing, oil, a powder foundation, an emulsion foundation, a wax foundation, a spray and the like, but is not limited thereto. In more detail, the cosmetic composition may be formulated as emollient toilet water, nourishing toilet water, nourishing cream, massage cream, essence, eye cream, cleansing cream, cleansing foam, cleansing water, pack, spray, or powder. In the case in which the formulation of the cosmetic composition of the present invention is a paste, a cream, or a gel, animal oil, vegetable oil, wax, paraffin, starch, cellulose derivatives, polyethylene glycol, silicon, bentonite, silica, talc, zinc oxide, or the like, may be used as a carrier ingredient. In the case in which the formulation of the cosmetic composition of the present invention is powder or spray, lactose, talc, silica, aluminum hydroxide, calcium silicate, or polyamide powder may be used as the carrier ingredient. Particularly, in the case in which the formulation is spray, the cosmetic composition may additionally contain a propellant such as chlorofluorohydrocarbon, propane/butane, or dimethylether. In the case in which the formulation of the cosmetic composition of the present invention is a solution or an emulsion, a solvent, a dissolving gent, or emulsifier is used as the carrier ingredient. For example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan may be used. In the case in which the formulation of the cosmetic composition of the present invention is a suspension, a liquid diluent such as water, ethanol, or propylene glycol, ethoxylated isostearyl alcohol, a suspending agent such as polyoxyethylene sorbitol ester and polyoxyethylene sorbitan ester, microcrystalline cellulose, aluminum methahydroxide, bentonite, agar and the like may be used as the carrier ingredient. In the case in which the formulation of the cosmetic composition of the present invention is a surfactant-containing cleansing, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamide, vegetable oils, lanoline derivatives, ethoxylated glycerol fatty acid ester, or the like, may be used as the carrier ingredient. In addition, the cosmetic composition for hair care according to the present invention may contain at least one general additive such as a suitable carrier, a surfactant, a fragrance, an opacifier, combining aids, protein, an aerosol propellants, a gelling agent, or the like, and be variously formulated as a shampoo, a rinse, wax for fixing hair, conditioner for hair care, and the like in addition to the copolymer.

A makeup method according to the present invention means all of the makeup methods of applying the cosmetic composition of the present invention onto human skin. That is, all of the makeup methods of applying the cosmetic composition onto skin known in the art pertain to the makeup method according to the present invention. The cosmetic composition according to the present invention may be applied alone, repeatedly applied, or applied together with another cosmetic composition different from the cosmetic composition of the present invention. In addition, the cosmetic composition according to the present invention having an excellent skin protection effect may be used according to the general using method and a usage frequency thereof may be changed according to a skin state or a taste of a user. In the case in which the formulation of the cosmetic composition according to the present invention is a soap or a surfactant-containing or surfactant-free cleansing, the composition may be cleansed, peeled off, or cleansed with water after being applied onto the skin. As a specific example, the soap may be a liquid soap, a powder soap, a solid soap, or a oil soap, the surfactant containing cleansing formulation may be a cleansing foam, cleansing water, a cleansing towel, or a cleansing pack, and the surfactant free cleansing formulation may be a cleansing cream, a cleansing lotion, cleansing water, or a cleansing gel, but the present invention is not limited thereto. Through the makeup method of applying the cosmetic composition containing the active ingredient according to the present invention onto the human skin, the skin moisturizing effect and atopic dermatitis alleviating effect may be obtained.

Hereinafter, preparation of the copolymer according to the present invention and the cosmetic composition using the prepared copolymer will be described through Preparation Examples and Examples, but the present invention is not limited thereto. In addition, various modifications and changes made by those skilled in the art are included in the present invention.

Preparation Example 1

Preparation of Copolymer 1200 g of an organic solvent obtained by mixing cyclohexane and ethylacetate with each other at a weight ratio of 50:50, 100 g of acrylic acid, and 2 g of MPC were put into a reactor, and then the reactant was stirred so as to be dissolved while slowly raising a temperature in the reactor to 60° C., followed by purging the reactor with nitrogen for 30 minutes. In addition, 0.8 g of pentaerythritol triallyl ether as a cross-linking agent and 0.04 g of Vazo 52 (Dupont) as a polymerization reaction initiator were dissolved in the 10 g of the organic solvent obtained by mixing cyclohexane and ethylacetate with each other at the weight ratio of 50:50 and put into the reactor when the temperature of the reactor approached at 60° C., followed by performing a polymerization reaction for 12 hours. After the polymerization reaction was terminated, the reactant was filtered and dried, thereby obtaining a copolymer as white powder.

A 0.5 weight % solution of the obtained copolymer had a neutral viscosity of 32,000 cps, and the transparency measured using a UV-vis. spectrometer (420, 10 cell) in a neutral state was 90%.

Preparation Example 2

Preparation of Copolymer 1200 g of an organic solvent obtained by mixing cyclohexane and ethylacetate with each other at a weight ratio of 50:50, 100 g of acrylic acid, and 1 g of MPC were put into a reactor, and then the reactant was stirred so as to be dissolved while slowly raising a temperature in the reactor to 60° C., followed by purging the reactor with nitrogen for 30 minutes. In addition, separately, 3 g of trimethylolpropane diallyl ether as a cross-linking agent and 0.04 g of Vazo 52 (Dupont) as a polymerization reaction initiator were dissolved in the 10 g of the organic solvent obtained by mixing cyclohexane and ethylacetate with each other at the weight ratio of 50:50, and put into the reactor when the temperature of the reactor approached at 60° C., followed by performing a polymerization reaction for hours. After the polymerization reaction was terminated, the filtered reaction product was put into a vacuum evaporator to remove the organic solvent at 90° C., thereby obtaining a copolymer as white powder. Describing physical properties of the obtained copolymer, a 0.5 weight % solution of the copolymer had a neutral viscosity of 30,000 cps, and the transparency measured using a UV-vis. spectrometer (420, 10 cell) in a neutralized state was 90%.

Preparation Example 3

Preparation of Copolymer 1200 g of a benzene organic solvent, 100 g of acrylic acid, and 10 g of MPC were put into a reactor, and then the reactant was stirred so as to be dissolved while slowly raising a temperature in the reactor to 80° C., followed by purging the reactor with nitrogen for 30 minutes. In addition, separately, 1.0 g of trimethylolpropane diallyl ether as a cross-linking agent and 0.2 g of azobisisobutyronitrile (AIBN) as a polymerization reaction initiator were dissolved in the 10 g of the benzene organic solvent, and put into the reactor when the temperature of the reactor approached at 80° C., followed by performing a polymerization reaction for 10 hours. After the polymerization reaction was terminated, the filtered reaction product was put into a vacuum evaporator to remove the organic solvent at 90° C., thereby obtaining a copolymer as white powder. Transparency of the obtained copolymer was 88%, and a 0.5 weight % aqueous solution of the copolymer had a neutral viscosity (viscosity at pH 7.0) of 22,000 cps.

Preparation Example 4

Preparation of Copolymer 1,400 g of an organic solvent obtained by mixing cyclohexane and ethylacetate with each other at a weight ratio of 50:50, 100 g of acrylic acid, and 20 g of MPC were put into a reactor, and then the reactant was stirred so as to be dissolved while slowly raising a temperature in the reactor to 70° C., followed by purging the reactor with nitrogen for 30 minutes. In addition, separately, 3 g of trimethylpropane diallyl ether as a cross-linking agent and 0.01 g of azobisisobutyronitrile (AIBN) as a polymerization reaction initiator were dissolved in the 5 g of the organic solvent obtained by mixing cyclohexane and ethylacetate with each other at the weight ratio of 50:50, and put into the reactor when the temperature of the reactor approached at 70° C., followed by performing a polymerization reaction for 10 hours. After the polymerization reaction was terminated, the filtered reaction product was put into a vacuum evaporator to remove the organic solvent at 90° C., thereby obtaining a copolymer as white powder. Transparency of the obtained copolymer was 92%, and a 0.5 weight % aqueous solution of the copolymer had a neutral viscosity (viscosity at pH 7.0) of 15,000 cps.

Preparation Example 5

Preparation of Copolymer 1,200 g of an organic solvent obtained by mixing cyclohexane and ethylacetate with each other at a weight ratio of 60:40, 100 g of acrylic acid, and 10 g of MPC were put into a reactor, and then the reactant was stirred so as to be dissolved while slowly raising a temperature in the reactor to 70° C., followed by purging the reactor with nitrogen for 30 minutes. In addition, separately, 1 g of diallyl pentaerythritol ether and 0.2 g of diallyl phthalate as cross-linking agents and 0.1 g of azobisisobutyronitrile (AIBN) as a polymerization reaction initiator were dissolved in the 10 g of the organic solvent obtained by mixing cyclohexane and ethylacetate with each other at the weight ratio of 60:40, and put into the reactor when the temperature of the reactor approached at 70° C., followed by performing a polymerization reaction for 10 hours. After the polymerization reaction was terminated, the filtered reaction product was put into a vacuum evaporator to remove the organic solvent at 90° C., thereby obtaining a copolymer as white powder. Transparency of the obtained copolymer was 90%, and a 0.5 weight % aqueous solution of the copolymer had a neutral viscosity (viscosity at pH 7.0) of 10,000 cps.

Preparation Example 6

Preparation of Copolymer 1,200 g of an organic solvent obtained by mixing cyclohexane and ethylacetate with each other at a weight ratio of 50:50, 100 g of acrylic acid, and 2 g of MPC were put into a reactor, and then the reactant was stirred so as to be dissolved while slowly raising a temperature in the reactor to 70° C., followed by purging the reactor with nitrogen for 30 minutes. In addition, separately, 3 g of trimethylolpropane diallyl ether as a cross-linking agent and 0.2 g of Vazo 52 (Dupont) as a polymerization reaction initiator were dissolved in the 10 g of the organic solvent obtained by mixing cyclohexane and ethylacetate with each other at the weight ratio of 50:50, and put into the reactor when the temperature of the reactor approached at 70° C., followed by performing a polymerization reaction for 10 hours. After the polymerization reaction was terminated, the filtered reaction product was put into a vacuum evaporator to remove the organic solvent at 90° C., thereby obtaining a copolymer as white powder.

Preparation Example 7

Preparation of Copolymer 1,200 g of an organic solvent obtained by mixing cyclohexane and ethylacetate with each other at a weight ratio of 50:50, 90 g of acrylic acid, 4 g of lauryl acrylate, and 3 g of MPC were put into a reactor, and then the reactant was stirred so as to be dissolved while slowly raising a temperature in the reactor to 70° C., followed by purging the reactor with nitrogen for 30 minutes. In addition, separately, 0.6 g of trimethylolpropane diallyl ether as a cross-linking agent and 0.04 g of Vazo 52 (Dupont) as a polymerization reaction initiator were dissolved in the 10 g of the organic solvent obtained by mixing cyclohexane and ethylacetate with each other at the weight ratio of 50:50, and put into the reactor when the temperature of the reactor approached at 70° C., followed by performing a polymerization reaction for 10 hours. After the polymerization reaction was terminated, the filtered reaction product was put into a vacuum evaporator to remove the organic solvent at 100° C., thereby obtaining a copolymer as white powder. Transparency of the obtained copolymer was 90%, and a 0.5 weight % aqueous solution had a neutral viscosity (viscosity at pH 7.0) of 7,000 cps.

Preparation Example 8

Preparation of Copolymer 1,200 g of an organic solvent obtained by mixing cyclohexane and ethylacetate with each other at a weight ratio of 50:50, 80 g of acrylic acid, 8 g of stearyl methacrylate, and 5 g of MPC were put into a reactor, and then the reactant was stirred so as to be dissolved while slowly raising a temperature in the reactor to 70° C., followed by purging the reactor with nitrogen for 30 minutes. In addition, separately, 0.9 g of trimethylolpropane diallyl ether as a cross-linking agent and 0.04 g of Vazo 52 (Dupont) as a polymerization reaction initiator were dissolved in the 10 g of the organic solvent obtained by mixing cyclohexane and ethylacetate with each other at the weight ratio of 50:50, and put into the reactor when the temperature of the reactor approached at 70° C., followed by performing a polymerization reaction for hours. After the polymerization reaction was terminated, the filtered reaction product was put into a vacuum evaporator to remove the organic solvent at 100° C., thereby obtaining a copolymer as white powder. Transparency of the obtained copolymer was 85%, and a 0.5 weight % aqueous solution has a neutral viscosity (viscosity at pH 7.0) of 27,000 cps.

Preparation Example 9

Preparation of Copolymer 1200 g of n-hexane, 100 g of acrylic acid, and 10 g of MPC were put into a reactor, and then the reactant was stirred so as to be dissolved while slowly raising a temperature in the reactor to 70° C., followed by purging the reactor with nitrogen for 30 minutes. In addition, separately, 3 g of trimethylolpropane diallyl ether as a cross-linking agent and 0.2 g of Vazo 52 (Dupont) as a polymerization reaction initiator were dissolved in the 10 g of n-hexane, and put into the reactor when the temperature of the reactor approached at 60° C., followed by performing a polymerization reaction for 10 hours. After the polymerization reaction was terminated, the filtered reaction product was put into a vacuum evaporator to remove the organic solvent at 90° C., thereby obtaining a copolymer as white powder. Describing physical properties of the obtained copolymer, a 0.5 weight % solution of the copolymer had a neutral viscosity of 25,000 cps, and the transparency measured using a UV-vis. spectrometer (420, 10 cell) in a neutralized state was 90%.

Comparative Preparation Example 1

1,200 g of an organic solvent obtained by mixing cyclohexane and ethylacetate with each other at a weight ratio of 40:60 and 100 g of acrylic acid were put into a reactor, and then the reactant was stirred so as to be dissolved while slowly raising a temperature in the reactor to 70° C., followed by purging the reactor with nitrogen for minutes. In addition, separately, 3 g of trimethylolpropane diallyl ether as a cross-linking agent and 0.04 g of Vazo 52 (Dupont) as a polymerization reaction initiator were dissolved in the 10 g of the organic solvent obtained by mixing cyclohexane and ethylacetate with each other at the weight ratio of 40:60, and put into the reactor when the temperature of the reactor approached at 70° C., followed by performing a polymerization reaction for hours. After the polymerization reaction was terminated, the filtered reaction product was put into a vacuum evaporator to remove the organic solvent at 100° C., thereby obtaining a cross-linked copolymer as white powder. Transparency of the obtained cross-linked copolymer was 90%, and a 0.5 weight % aqueous solution had a neutral viscosity (viscosity at pH 7.0) of 34,000 cps.

Comparative Preparation Example 2

1200 g of a benzene organic solvent and 100 g of acrylic acid were put into a reactor, and then the reactant was stirred so as to be dissolved while slowly raising a temperature in the reactor to 80° C., followed by purging the reactor with nitrogen for 30 minutes. In addition, separately, 3 g of trimethylolpropane diallyl ether as a cross-linking agent and 0.05 g of Vazo 52 (Dupont) as a polymerization reaction initiator were dissolved in the 10 g of the benzene organic solvent, and put into the reactor when the temperature of the reactor approached at 80° C., followed by performing a polymerization reaction for 5 hours. After the polymerization reaction was terminated, the filtered reaction product was put into a vacuum evaporator to remove the organic solvent at 100° C., thereby obtaining a cross-linked copolymer as white powder. Transparency of the obtained cross-linked copolymer was 90%, and a 0.5 weight % aqueous solution had a neutral viscosity (viscosity at pH 7.0) of 36,000 cps.

Comparative Preparation Example 3

1,200 g of an organic solvent obtained by mixing cyclohexane and ethylacetate with each other at a weight ratio of 20:80 and 100 g of acrylic acid were put into a reactor, and then the reactant was stirred so as to be dissolved while slowly raising a temperature in the reactor to 70° C., followed by purging the reactor with nitrogen for 30 minutes. In addition, separately, 0.04 g of Vazo 52 (Dupont) as a polymerization reaction initiator was dissolved in the 10 g of the organic solvent obtained by mixing cyclohexane and ethylacetate with each other at the weight ratio of 20:80, and put into the reactor when the temperature of the reactor approached at 70° C., followed by performing a polymerization reaction for 10 hours. After the polymerization reaction was terminated, the filtered reaction product was put into a vacuum evaporator to remove the organic solvent at 100° C., thereby obtaining a copolymer as white powder. Transparency of the obtained copolymer was 95%, and a 0.5 weight % aqueous solution has a neutral viscosity (viscosity at pH 7.0) of 100 cps.

Example 1

Emollient Toilet Water (Skin Lotion)

The emollient toilet water was prepared by mixing constituent ingredients at a constituent ratio shown in the following Table 1 using the copolymer prepared in Preparation Example 1. Thereafter, a moisturizing effect, a skin barrier function improving effect, and an inflammation alleviating effect of a cosmetic material were evaluated using this emollient toilet water, and the results were shown in Table 2 (moisturizing effect and skin barrier function improving effect) and Table 3 (inflammatory alleviating effect). A method of evaluating each effect was as follows.

Moisturizing and Skin Barrier Function Improving Effect
After 30 healthy women were divided into four groups (A, B, C) in a room with no air flow at 25° C. and relative humidity of 45%, the cosmetic material of Example 1, the cosmetic material of Comparative Example 1, and the cosmetic material of Comparative Example 2 were formulated as shown in Table 1 and applied onto forearms of women in the A group, B group, and C group three times a day for 6 weeks, respectively. Thereafter, transepidermal water loss (TEWL) values were measured using a TEWAMETER TM300 (C+K Electronic GmbH. Germany) as TEWL value change amounts according to the time, and a water content of the skin was digitized between 0 to 150 according to the electrical conductivity change depending on the epidermal water content using a CORNEOMETER CM 820 PC(C+K Electronic GmbH. Germany), thereby measuring a moisturizing effect.

Inflammation Alleviating Effect
First, a close patch test was performed on 30 women for 4 hours by applying a 5% sodium dodecyl sulfate (SDS) solution onto application sites of the cosmetic material to be tested, and 30 women were divided into 3 groups. Then, the cosmetic material of Example 1, the cosmetic material of Comparative Example 1, and the cosmetic material of Comparative Example 3 were formulated as shown in Table 1 and applied (2 times/day, 0.2 g/one-time) onto areas (2×2) in left forearms of women in the A group, B group, and C group for 2 weeks, respectively. Thereafter, a degree of alleviating inflammation caused by applying SDS was measured by measuring a degree of skin erythema using a Mexameter MX18 (C+K Electronic GmbH. Germany).

Comparative Example 1

Composition of Emollient Toilet Water

The composition was prepared so as to contain the ingredients shown in Table 1 by the same method as in Example 1 except for not using the copolymer of Example 1, and effects thereof were measured. The results were shown in Tables 2 and 3.

Comparative Example 2

Composition of Emollient Toilet Water

The composition was prepared so as to contain the ingredients shown in Table 1 by the same method as in Example 1 except for using hyaluronic acid, which was an existing material used in the art, instead of the copolymer of Example 1 at the same content, and effects thereof were measured. The results were shown in Tables 2 and 3.

Comparative Example 3

Composition of Emollient Toilet Water

The composition was prepared so as to contain the ingredients shown in Table 1 by the same method as in Example 1 except for using Witch hazel ext. (Dragoco), which was an existing material used in the art, instead of the copolymer of Example 1 at the same content, and effects thereof were measured. The results were shown in Tables 2 and 3.

TABLE 1

Composition of emollient toilet water

| Ingredient | Content (weight %) | | | |
| --- | --- | --- | --- | --- |
| | Example 1 | Comparative Example 1 | Comparative Example 2 | Comparative Example 3 |
| Copolymer in Preparation Example 1 | 0.3 | — | — | — |
| Hyaluronic acid | — | — | 0.3 | — |
| Witch hazel extract | — | — | — | 0.3 |
| Vaseline | 7.0 | 7.0 | 7.0 | 7.0 |
| Liquid paraffin | 10.0 | 10.0 | 10.0 | 10.0 |
| Bees wax | 2.0 | 2.0 | 2.0 | 2.0 |
| Polysorbate 60 | 2.0 | 2.0 | 2.0 | 2.0 |
| Sorbitan sesquioleate | 2.5 | 2.5 | 2.5 | 2.5 |
| Squalan | 3.0 | 3.0 | 3.0 | 3.0 |
| Propyleneglycol | 6.0 | 6.0 | 6.0 | 6.0 |
| Glycerin | 4.0 | 4.0 | 4.0 | 4.0 |
| triethanolamine | 0.5 | 0.5 | 0.5 | 0.5 |
| Carboxyvinylpolymer | 0.5 | 0.5 | 0.5 | 0.5 |
| Tocopherylacetate | 0.1 | 0.1 | 0.1 | 0.1 |
| Fragrance | 0.01 | 0.01 | 0.01 | 0.01 |
| Purified water | to 100 | to 100 | to 100 | to 100 |

TABLE 2

Moisturizing and skin barrier function improving effects of emollient toilet water

| | ΔTEWL | Corneometer value |
| --- | --- | --- |
| Example 1 | 1.2 | 120 |
| Comparative Example 1 | 6.1 | 86 |
| Comparative Example 2 | 2.3 | 111 |

As shown in Table 2, in the case of using the cosmetic material (Example 1) containing the copolymer according to the present invention, a transepidermal water loss (TEWL) value may be significantly reduced as compared to the case of using the cosmetic material (Comparative Example 1) not containing the copolymer and the case of using the cosmetic material (Comparative Example 2) containing only hyaluronic acid. Therefore, it may be appreciated that the copolymer has a moisturizing effect. Further, it may be appreciated that in Example 1, a corneometer value obtained by measuring the water content of the skin was significantly increased as compared to Comparative Examples 1 to 3-2. That is, in the case of using the cosmetic material containing the copolymer according to the present invention, the water content of the skin was highly measured, and the transepidermal water loss also was improved. Therefore, it may be appreciated that the cosmetic material containing the copolymer according to the present invention had significantly excellent moisturizing and skin barrier function improving effects.

TABLE 3

Inflammation alleviating effect

| Example 1 | Erythema index | Comparative Example 1 | Erythema index | Comparative Example 3 | Erythema index |
|---|---|---|---|---|---|
| Subject 1 | 180 | Subject 11 | 331 | Subject 21 | 250 |
| Subject 2 | 215 | Subject 12 | 318 | Subject 22 | 277 |
| Subject 3 | 230 | Subject 13 | 296 | Subject 23 | 255 |
| Subject 4 | 167 | Subject 14 | 277 | Subject 24 | 210 |
| Subject 5 | 155 | Subject 15 | 350 | Subject 25 | 211 |
| Subject 6 | 141 | Subject 16 | 387 | Subject 26 | 233 |
| Subject 7 | 177 | Subject 17 | 376 | Subject 27 | 245 |
| Subject 8 | 230 | Subject 18 | 336 | Subject 28 | 236 |
| Subject 9 | 228 | Subject 19 | 342 | Subject 29 | 229 |
| Subject 10 | 130 | Subject 20 | 251 | Subject 30 | 265 |
| Average | 185.3 | Average | 326.4 | Average | 241.1 |

As shown in Table 3, it may be appreciated that the cosmetic material (Example 1) containing the copolymer according to the present invention had a more excellent inflammation alleviating effect as compared to the cosmetic material not containing the copolymer according to the present invention and the cosmetic material containing the Witch hazel extract according to the related art.

Example 2

Composition for Hair Care 40.05 g of water was put into a mixing tank and 0.8 g of the copolymer prepared in Preparation Example 1 was put thereinto while raising a temperature. Then, 1 g of propylene glycol (PG) was put thereinto and the temperature was raised to 75° C. 18 g of sodium lauryl sulfate, 17 g of sodium laureth sulfate, 2.5 g of cocofatty acid diethanolamide, 8 g of cocamido propyl betaine, 3 g of soyamidopropylamine oxide, 0.5 g of cetearyl alcohol, 2 g of disodium Cocoamphodiacetate, 0.6 g of ethylene glycol distearate) 2 g of polyglyceryl-2 caprate, 2 g of DC5-7137 emulsion (Dimethicone & cocamido propyl betaine & C12-15 parath-3, Dow Corning Corp.), and 0.05 g of tetrasodium EDTA were put into the mixing tank to mix them at 75° C. for about 30 minutes until a uniform mixture was obtained, and then the temperature was cooled to 45° C. Next, 0.05 g of alantoin, 0.05 g of methyl chloroisothiazolinone & Methyl isothiazolinone, 0.1 g of DL-panthenol, 0.5 g of citric acid, and 0.3 g of fragrance were put into the mixing tank to mix them at 45° C. until the mixture became uniform, thereby preparing 100 g of the composition for hair care.

After the prepared composition for hair care was kept at room temperature for 30 days, phase stability was evaluated by observing whether or not the phase was separated by the naked eyes, and sensory properties of the composition were performed on 10 women in their 20 s. As evaluation items, a application feeling (spreadability), feeling at the time of washing the hair, combing hair in a wet state, combing hair after drying hair, volume of hair, and gloss of hair were relatively evaluated. The result was compared to Comparative Examples and shown in Tables 5 to 10. As a result, it may be appreciated that in the case of using the copolymer according to the present invention as the constituent ingredient, on average, the sensory properties were significantly excellent as compared to the case of not using the composition or using another material, such that the copolymer according to the present invention may exhibit excellent properties in the cosmetic material.

Example 3

Composition for Hair Care

The composition for hair care was prepared by the same method as in Example 2 except for using the copolymer prepared in Preparation Example 8 instead of the copolymer prepared in Preparation Example 1. The results were shown in Tables 4 to 10.

Example 4

Composition for Hair Care

The composition for hair care was prepared by the same method as in Example 2 except for using the copolymer prepared in Preparation Example 3 instead of the copolymer prepared in Preparation Example 1. The results were shown in Tables 4 to 10.

Example 5

Composition for Hair Care

The composition for hair care was prepared by the same method as in Example 2 except for using the copolymer prepared in Preparation Example 4 instead of the copolymer prepared in Preparation Example 1. The results were shown in Tables 4 to 10.

Comparative Example 4

Composition for hair Care

The composition for hair care was prepared by the same method as in Example 2 except for using the copolymer prepared in Comparative Preparation Example 1 instead of the copolymer prepared in Preparation Example 1. The results were shown in Tables 4 to 10.

Comparative Example 5

Composition for Hair Care

The composition for hair care was prepared by the same method as in Example 82 except for using the copolymer prepared in Comparative Preparation Example 2 instead of the copolymer prepared in Preparation Example 1. The results were shown in Tables 4 to 10.

Comparative Example 6

Composition for Hair Care

The composition for hair care was prepared by the same method as in Example 2 except for using the copolymer prepared in Comparative Preparation Example 3 instead of the copolymer prepared in Preparation Example 1. The results were shown in Tables 4 to 10.

TABLE 4

Evaluation of phase stability

| | Example 2 | Example 3 | Example 4 | Example 5 | Comparative Example 4 | Comparative Example 5 | Comparative Example 6 |
|---|---|---|---|---|---|---|---|
| Phase stability | ○ | ○ | ○ | ○ | ○ | ○ | X |

○: phase is not separated,
X: phase is separated

TABLE 5

Application feeling (spreadability)

| Pane 1 | Example 3 | Example 4 | Example 5 | Example 6 | Comparative Example 4 | Comparative Example 5 | Comparative Example 6 |
|---|---|---|---|---|---|---|---|
| PJH | 10 | 10 | 10 | 10 | 8 | 8 | 5 |
| MJL | 8 | 10 | 10 | 8 | 5 | 8 | 3 |
| LSY | 10 | 10 | 10 | 8 | 8 | 5 | 1 |
| LMI | 10 | 10 | 10 | 5 | 8 | 5 | 5 |
| SSM | 8 | 10 | 10 | 10 | 10 | 8 | 5 |
| PYS | 10 | 10 | 10 | 8 | 8 | 5 | 3 |
| HYA | 8 | 10 | 10 | 10 | 5 | 5 | 5 |
| KJH | 10 | 10 | 8 | 8 | 5 | 5 | 3 |
| YSS | 8 | 10 | 10 | 5 | 8 | 5 | 3 |
| KJK | 8 | 10 | 10 | 8 | 5 | 5 | 1 |

10: Very good/
8: Good/
5: Fair/
3: Poor/
1: Very poor

TABLE 6

Feeling at the time of washing the hair

| Pane 1 | Example 3 | Example 4 | Example 5 | Example 6 | Comparative Example 4 | Comparative Example 5 | Comparative Example 6 |
|---|---|---|---|---|---|---|---|
| PJH | 10 | 10 | 10 | 10 | 8 | 8 | 5 |
| MJL | 10 | 10 | 10 | 8 | 5 | 5 | 3 |
| LSY | 10 | 10 | 10 | 10 | 8 | 5 | 1 |
| LMI | 10 | 10 | 8 | 8 | 8 | 5 | 3 |
| SSM | 8 | 10 | 10 | 10 | 8 | 8 | 5 |
| PYS | 10 | 10 | 10 | 8 | 8 | 5 | 3 |
| HYA | 8 | 10 | 10 | 10 | 5 | 5 | 5 |
| KJH | 10 | 10 | 8 | 10 | 5 | 5 | 3 |
| YSS | 8 | 10 | 10 | 10 | 5 | 3 | 1 |
| KJK | 5 | 10 | 10 | 8 | 5 | 5 | 1 |

10: Very good/
8: Good/
5: Fair/
3: Poor/
1: Very poor

TABLE 7

Combing hair in a wet state

| Pane 1 | Example 3 | Example 4 | Example 5 | Example 6 | Comparative Example 4 | Comparative Example 5 | Comparative Example 6 |
|---|---|---|---|---|---|---|---|
| PJH | 10 | 10 | 10 | 10 | 5 | 5 | 3 |
| MJL | 8 | 10 | 10 | 8 | 5 | 8 | 3 |
| LSY | 8 | 10 | 8 | 10 | 8 | 5 | 1 |
| LMI | 10 | 10 | 8 | 10 | 5 | 5 | 5 |
| SSM | 8 | 10 | 10 | 10 | 5 | 8 | 3 |
| PYS | 8 | 10 | 10 | 8 | 8 | 5 | 1 |
| HYA | 8 | 10 | 10 | 10 | 5 | 5 | 5 |

TABLE 7-continued

Combing hair in a wet state

| Pane 1 | Example 3 | Example 4 | Example 5 | Example 6 | Comparative Example 4 | Comparative Example 5 | Comparative Example 6 |
|---|---|---|---|---|---|---|---|
| KJH | 10 | 10 | 10 | 8 | 5 | 8 | 3 |
| YSS | 8 | 10 | 10 | 8 | 8 | 5 | 3 |
| KJK | 10 | 10 | 10 | 10 | 5 | 5 | 1 |

10: Very good/
8: Good/
5: Fair/
3: Poor/
1: Very poor

TABLE 8

Combing hair after drying hair

| Pane 1 | Example 3 | Example 4 | Example 5 | Example 6 | Comparative Example 4 | Comparative Example 5 | Comparative Example 6 |
|---|---|---|---|---|---|---|---|
| PJH | 8 | 10 | 10 | 10 | 8 | 5 | 3 |
| MJL | 8 | 8 | 10 | 10 | 5 | 5 | 3 |
| LSY | 10 | 10 | 10 | 8 | 5 | 5 | 1 |
| LMI | 8 | 10 | 10 | 10 | 8 | 3 | 3 |
| SSM | 8 | 10 | 10 | 10 | 3 | 8 | 3 |
| PYS | 10 | 10 | 10 | 10 | 5 | 5 | 3 |
| HYA | 8 | 10 | 10 | 10 | 8 | 5 | 5 |
| KJH | 10 | 10 | 10 | 10 | 5 | 5 | 1 |
| YSS | 10 | 10 | 10 | 10 | 5 | 3 | 3 |
| KJK | 10 | 10 | 8 | 8 | 5 | 5 | 1 |

10: Very good/
8: Good/
5: Fair/
3: Poor/
1: Very poor

TABLE 9

Volume of hair

| Pane 1 | Example 3 | Example 4 | Example 5 | Example 6 | Comparative Example 4 | Comparative Example 5 | Comparative Example 6 |
|---|---|---|---|---|---|---|---|
| PJH | 10 | 10 | 10 | 10 | 8 | 5 | 3 |
| MJL | 8 | 10 | 8 | 8 | 3 | 8 | 3 |
| LSY | 8 | 10 | 10 | 10 | 5 | 5 | 1 |
| LMI | 8 | 10 | 10 | 10 | 8 | 3 | 3 |
| SSM | 8 | 10 | 10 | 10 | 8 | 8 | 5 |
| PYS | 10 | 10 | 10 | 8 | 8 | 5 | 1 |
| HYA | 10 | 8 | 10 | 10 | 5 | 5 | 3 |
| KJH | 10 | 10 | 10 | 10 | 5 | 3 | 3 |
| YSS | 8 | 10 | 10 | 10 | 5 | 3 | 3 |
| KJK | 8 | 10 | 10 | 8 | 3 | 5 | 1 |

10: Very good/
8: Good/
5: Fair/
3: Poor/
1: Very poor

TABLE 10

Gloss of hair

| Pane 1 | Example 3 | Example 4 | Example 5 | Example 6 | Comparative Example 4 | Comparative Example 5 | Comparative Example 6 |
|---|---|---|---|---|---|---|---|
| PJH | 10 | 10 | 10 | 10 | 8 | 5 | 3 |
| MJL | 10 | 10 | 10 | 10 | 5 | 8 | 5 |
| LSY | 10 | 10 | 10 | 10 | 8 | 3 | 1 |
| LMI | 10 | 10 | 10 | 8 | 3 | 5 | 3 |
| SSM | 5 | 10 | 10 | 10 | 5 | 5 | 3 |
| PYS | 10 | 10 | 10 | 10 | 8 | 5 | 1 |

TABLE 10-continued

Gloss of hair

| Pane 1 | Example 3 | Example 4 | Example 5 | Example 6 | Comparative Example 4 | Comparative Example 5 | Comparative Example 6 |
|---|---|---|---|---|---|---|---|
| HYA | 8 | 10 | 10 | 10 | 8 | 3 | 3 |
| KJH | 10 | 10 | 10 | 8 | 5 | 5 | 1 |
| YSS | 8 | 10 | 10 | 10 | 5 | 5 | 3 |
| KJK | 8 | 10 | 10 | 10 | 5 | 5 | 1 |

10: Very good/
8: Good/
5: Fair/
3: Poor/
1: Very poor

Hereinafter, uses of the cosmetic composition according to the present invention will be additionally described with reference to various examples prepared as various formulations. It may be appreciated that in the case of using the copolymer according to the present invention, the physical properties were excellent. In addition, it may be appreciated by those skilled in the art that all of the cosmetic compositions using the copolymer according to the present invention pertains to the scope of the present invention.

Example 7

Another Example of Emollient Toilet Water (Skin Lotion)

Tests were performed on a composition of skin lotion having constituent ingredients different from those in Example 1 as shown in the following Table 11, and as a result, it may be confirmed that the composition had effects similar to those of the composition in Example 1.

TABLE 11

Composition of emollient toilet water (skin lotion)

| Ingredient | Content (weight %) |
|---|---|
| Copolymer in Preparation Example 1 | 0.3 |
| Glycerin | 5.0 |
| 1,3-butyleneglycol | 3.0 |
| PEG 1500 | 1.0 |
| Allantoin | 0.1 |
| DL-panthenol | 0.3 |
| Benzophenone-9 | 0.04 |
| EDTA-2Na | 0.02 |
| Sodium hyaluronate | 5.0 |
| Ethanol | 10.0 |
| Octyldodeceth-16 | 0.2 |
| Polysorbate 20 | 0.2 |
| Fragrance | 0.02 |
| Purified water | to 100 |

Example 8

Nourishing Toilet Water (Milk Lotion)

The nourishing toilet water was prepared by a general method so as to have constituent ingredients shown in Table 12. As a result, it may be appreciated that effects thereof were similar to those as described above.

TABLE 12

Composition of nourishing toilet water (milk lotion)

| Ingredient | Content (weight %) |
|---|---|
| Copolymer in Preparation Example 1 | 0.3 |
| Glyceryl stearate SE | 1.5 |
| Stearyl alcohol | 1.5 |
| Lanoline | 1.3 |
| Polysorbate 60 | 0.3 |
| Sorbitan stearate | 0.5 |
| Hydrogenated vegetable oil | 1.0 |
| Mineral oil | 5.0 |
| Squalan | 3.0 |
| Trioctanoin | 2.0 |
| Dimethicone | 0.8 |
| Carboxyvinylpolymer | 0.12 |
| Glycerin | 5.0 |
| 1,3-butyleneglycol | 3.0 |
| Sodium hyaluronate | 2.0 |
| triethanolamine | 0.12 |
| Fragrance | 0.01 |
| Purified water | to 100 |

Example 9

Nourishing Cream

The nourishing cream was prepared by a general method so as to have constituent ingredients shown in Table 13. As a result, it may be appreciated that effects thereof were similar to those as described above. In addition, in view of feeling after use, the nourishing cream had excellent properties in that the nourishing cream was soft, well spread, and kept the skin moist for a long time without being sticky.

TABLE 13

Composition of nourishing cream

| Ingredient | Content (weight %) |
|---|---|
| Copolymer in Preparation Example 1 | 0.3 |
| Lipophilic glyceryl Monostearate | 2.0 |
| Stearyl alcohol | 2.2 |
| Stearic acid | 1.5 |
| Polysorbate 60 | 1.5 |
| Sorbitan stearate | 0.6 |
| Hydrogenated vegetable oil | 1.0 |
| Mineral oil | 5.0 |
| Squalan | 3.0 |
| Trioctanoin | 2.0 |
| Dimethicone | 1.2 |
| Sodium magnesium silicate | 0.1 |
| Glycerin | 5.0 |
| 1,3-butyleneglycol | 3.0 |

TABLE 13-continued

Composition of nourishing cream

| Ingredient | Content (weight %) |
|---|---|
| Sodium hyaluronate | 2.0 |
| triethanolamine | 1.0 |
| Fragrance | 0.02 |
| Purified water | to 100 |

Example 9

Massage Cream

The massage cream was prepared by a general method so as to have constituent ingredients shown in Table 14. As a result, it may be appreciated that effects thereof were similar to those as described above. In addition, in view of feeling after use, when a massage was performed using this massage cream, excellent feeling after use such as smooth and sufficient feelings were obtained.

TABLE 14

Composition of massage cream

| Ingredient | Content (weight %) |
|---|---|
| Copolymer in Preparation Example 1 | 0.3 |
| Lipophilic glyceryl Monostearate | 1.5 |
| Stearyl alcohol | 1.5 |
| Stearic acid | 1.0 |
| Polysorbate 60 | 1.5 |
| Sorbitan stearate | 0.6 |
| Isostearyl siostearate | 5.0 |
| Minerals | 35.0 |
| Squalan | 5.0 |
| Dimethicone | 0.5 |
| Hydroxyethyl cellulose | 0.12 |
| Glycerin | 6.0 |
| triethanolamine | 0.7 |
| Fragrance | 0.01 |
| Purified water | to 100 |

Example 10

Comparative Examples 7 to 9

Essence

The nourishing toilet water essence was prepared by a general method so as to have constituent ingredients shown in Table 15, and effects thereof were shown in Table 16. The physical properties were measured as follows.

Test Method

1. An inner site of forearm of a subject was treated with a 5% sodium dodecyl sulfate (SDS) solution for 5 minutes and dried.
2. After 1 hour, a water content of the skin, an erythema index, and a TEWL at the test sites were measured. These measurement values were considered as initial measurement values.
3. The 5% SDS solution was applied once a day, and a test sample was applied twice a day onto the test site.
4. Application of the test sample was performed after 2 hours and 6 hours of application of the 5% SDS solution. 5. After the test sample was applied for 2 week, the water content of the skin, erythema, and a TEWL at each test site were measured. These measurement values were considered as final measurement values.
6. The skin improving effect of each of samples were evaluated by comparing the final measurement values and the initial measurement values at each test site with each other.
7. Skin measurement was performed 5 times at each test site, and an average value thereof was selected. Among the test items, the TEWL was measured using a TEWAMETER TM300(C+K Electronic GmbH. Germany), the epidermal water content was measured using a CORNEOMETER CM 820 PC(C+K Electronic GmbH. Germany), and the erythema index was measured using a Mexameter MX18 (C+K Electronics GmbH. Germany). Then, change rates thereof were calculated according to the following Calculation Equation.

Change rate(%)=(final measurement value−initial measurement value)/(initial measurement value)*100

TABLE 15

Composition of essence

| | Content (weight %) | | | |
|---|---|---|---|---|
| Ingredient | Example 10 | Comparative Example 7 | Comparative Example 8 | Comparative Example 9 |
| Copolymer in Preparation Example 1 | 0.3 | — | — | — |
| Hyaluronic acid | — | — | 0.3 | — |
| Witch hazel extract | — | — | — | 0.3 |
| Glycerin | 10.0 | 10.0 | 10.0 | 10.0 |
| Betaine | 5.0 | 5.0 | 5.0 | 5.0 |
| PEG 1500 | 2.0 | 2.0 | 2.0 | 2.0 |
| Allantoin | 0.1 | 0.1 | 0.1 | 0.1 |
| DL-panthenol | 0.3 | 0.3 | 0.3 | 0.3 |
| EDTA-2Na | 0.02 | 0.02 | 0.02 | 0.02 |
| Benzophenone-9 | 0.04 | 0.04 | 0.04 | 0.04 |
| Hydroxyethyl cellulose | 0.1 | 0.1 | 0.1 | 0.1 |
| Sodium hyaluronate | 8.0 | 8.0 | 8.0 | 8.0 |
| Carboxyvinylpolymer | 0.2 | 0.2 | 0.2 | 0.2 |
| Triethanolamine | 0.18 | 0.18 | 0.18 | 0.18 |
| Octyldodecanol | 0.3 | 0.3 | 0.3 | 0.3 |
| Octyldodeceth 16 | 0.4 | 0.4 | 0.4 | 0.4 |
| Ethanol | 6.0 | 6.0 | 6.0 | 6.0 |
| Fragrance | 0.02 | 0.02 | 0.02 | 0.02 |
| Purified water | to 100 | to 100 | to 100 | to 100 |

TABLE 16

Evaluation results of composition of essence

| Physical property | Example 10 | Comparative Example 7 | Comparative Example 8 |
|---|---|---|---|
| Skin moisture change rate (%) | 70 | −31 | 69 |
| Erthema change rate (%) | −12.4 | 9.5 | −10.2 |
| Transepidermal water loss change rate (%) | 10.3 | 34.3 | 40.3 |

Evaluation was performed at a condition at which SDS was continuously applied to thereby continuously irritate the skin. Under this condition, skin barrier functions were damaged by irritation, such that erythema was increased, and the TEWL was increased due to the damage. As a result, the water content of the skin was decreased. Under the condition as described above, whether or not the essence has effects of replacing or recovering the skin barrier functions and maintaining water contained in the skin in addition to protecting the skin from irritation were judged by measuring three indexes before and after treatment of the essence. As shown in Table 16, all of the three indexes were most excellent in Example 10 containing the copolymer according to the present invention. Therefore, it may be appreciated that the copolymer had excellent effects of replacing or recovering the skin barrier functions and maintaining water contained in skin in addition to protecting the skin from irritation.

Example 11

Comparative Examples 10 to 11

Pack

The pack was prepared by a general method so as to have constituent ingredients as shown in Table 17, and effects thereof were excellent. Particularly, it was confirmed that a moisturizing effect and a moisturizing effect after cleansing were excellent, and the results were shown in the following Table 18. Performance evaluation was performed as follows. Each of the packs in Example 11 and Comparative Examples 10 and 11 was applied onto an inner site of forearm of a subject. After 1 hour, a water content of the skin was measured, and the test site was cleansed using flowing water. After 1 hour, the water content of the skin was measured again using the above-mentioned Coneometer.

TABLE 17

Composition of pack

| Ingredient | Content (weight %) | | |
|---|---|---|---|
| | Example 11 | Comparative Example 10 | Comparative Example 11 |
| Copolymer in Preparation Example 1 | 0.3 | — | — |
| Hyaluronic acid | — | — | 0.3 |
| Polyvinylalcohol | 15.0 | 15.0 | 15.0 |
| Cellulose gum | 0.15 | 0.15 | 0.15 |
| Glycerin | 3.0 | 3.0 | 3.0 |
| PEG 1500 | 2.0 | 2.0 | 2.0 |
| DL-panthenol | 0.4 | 0.4 | 0.4 |
| Cyclodextrine | 0.15 | 0.15 | 0.15 |
| Allantoin | 0.1 | 0.1 | 0.1 |
| Glycyrrizin monoammonium | 0.3 | 0.3 | 0.3 |
| Nitcotinamide | 0.5 | 0.5 | 0.5 |
| Ethanol | 6.0 | 6.0 | 6.0 |
| PEG 40 hardening castor oil | 0.3 | 0.3 | 0.3 |
| Fragrance | 0.02 | 0.02 | 0.02 |
| Purified water | to 100 | to 100 | to 100 |

TABLE 18

Evaluation results of physical properties of pack

| Physical property | Example 11 | Comparative Example 10 | Comparative Example 11 |
|---|---|---|---|
| Skin moisture content | 60.4 | 50 | 22.3 |
| Skin moisture after cleaning | 40.3 | 25.1 | 20.2 |

As shown in Table 18, it may be appreciated that the pack of Example 11 containing the copolymer prepared in Preparation Example 1 has an excellent moisturizing effect after cleansing as well as a simple moisturizing effect.

The invention claimed is:

1. A copolymer comprising:
an α, β-ethylenically unsaturated monomer;
a phosphorylcholine monomer represented by the following Chemical Formula (1)

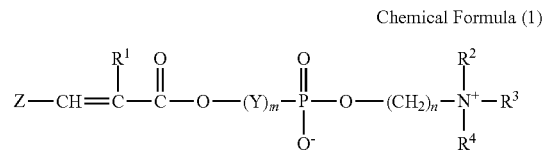

Chemical Formula (1)

where Z is a hydrogen atom or $R^5$—O—CO— (here, $R^5$ is a hydrogen atom, an alkyl group having 1 to 10 carbon atoms, or a hydroxyalkyl group having 1 to 10 carbon atoms), Y is an alkyleneoxy group having 1 to 20 carbon atoms, $R^1$ is a hydrogen atom or a hydrocarbon group having 1 to 5 carbon atoms, $R^2$, $R^3$ and $R^4$ each are independently a hydrogen atom, a hydrocarbon or hydroxy hydrocarbon group having 1 to 6 carbon atoms, m is an integer of 1 to 20, and n is an integer of 2 to 5; and
a cross-linking agent having at least two unsaturated ethylene bonding groups capable of being cross-linked with the phosphorylcholine monomer and the α, β-ethylenically unsaturated monomer as a monomer,
wherein the copolymer contains 0.1 to 80 parts by weight of the phosphorylcholine monomer and 0.01 to 30 parts by weight of the cross-linking agent, based on 100 parts by weight of the α, β-ethylenically unsaturated monomer.

2. The copolymer of claim 1, wherein the α,β-ethylenically unsaturated monomer further contains a material represented by the following Chemical Formula (2)

Chemical Formula (2)

where L is a hydrogen atom or $R^8$—O—CO—, $R^8$ is a hydrogen atom, an alkyl group having 1 to 10 carbon atoms, or an hydroxyalkyl group having 1 to 10 carbon atoms, X is any one selected from

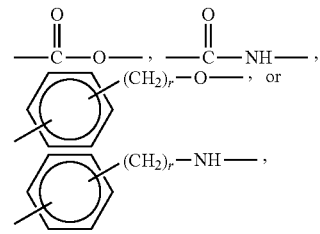

and r is an integer of 1 to 10, $R^6$ is a hydrogen atom, an alkyl group having 1 to 5 carbon atoms, a halogen atom, a hydroxy group, or a cyano group, and $R^7$ is a hydrogen atom or a hydrocarbon group having 1 to 30 carbon atoms.

3. The copolymer of claim 1, wherein the phosphorylcholine monomer is at least one selected from the group consisting of 2-((meth)acryloyloxy)ethyl-2'-(trimethylammonio)ethylphosphate, 3-((meth)acryloyloxy)propyl-2'-

(trimethylammonio)ethylphosphate, 4-((meth)acryloyloxy)butyl-2'-(trimethylammonio)ethylphosphate, 5-((meth)acryloyloxy)pentyl-2'-(trimethylammonio)ethylphosphate, 6-((meth)acryloyloxy)hexyl-2'-(trimethylammonio)ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethylphosphate, 2-((meth)acryloyloxy)propyl-2'-(trimethylammonio)ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethylphosphate, ethyl-(2'-trimethylammonio ethylphosphorylethyl)fumarate, butyl-(2'-trimethylammonio ethylphosphorylethyl)fumarate, hydroxyethyl-(T-trimethylammonio ethylphosphorylethyl)fumarate, ethyl-(2'-trimethylammonio ethylphosphorylethyl)fumarate, butyl-(2'-trimethylammonio ethylphosphorylethyl)fumarate and hydroxyethyl-(2'-trimethylammonio ethylphosphorylethyl)fumarate.

4. The copolymer of claim 1, wherein the cross-linking agent is one or at least two selected from a group consisting of ethylene glycol diacrylate, ethylene glycol dimethacrylate, propylene glycol diacrylate, propylene glycol dimethacrylate, butylene glycol diacrylate, butylene glycol dimethacrylate, hexylene glycol diacrylate, hexylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, allyl acrylate, allyl methacrylate, methallyl acrylate, allyl ethacrylate, ethallyl acrylate, methallyl methacrylate, diallyl phthalate, diallyl maleate, diallyl succinate, triallyl phosphate, diallyl oxalate, diallyl malonate, diallyl citrate, diallyl fumarate, divinyl benzene, trivinyl benzene, vinyl crotonate, N,N-methylene-bis-acrylamide, trimethylolpropane diallyl ether trimethylolpropane triallyl ether, diallyl pentaerythritol ether, triallyl pentaerythritol ether, tetraallyl pentaerythritol ether, diallyl sucrose ether, triallyl sucrose ether, tetraallyl sucrose ether, pentaallyl sucrose ether and hexaallyl sucrose ether.

5. A cosmetic composition comprising the copolymer of claim 1 as an active ingredient.

6. The cosmetic composition of claim 5, wherein it is a cosmetic composition for moisturizing skin, improving skin barrier functions, alleviating atopic dermatitis, or alleviating inflammation.

7. The cosmetic composition of claim 5, wherein it is a cosmetic composition for hair care in order to impart spreadability and a hair conditioning effect.

8. The cosmetic composition of claim 5, wherein a content of the copolymer in the cosmetic composition is 0.001 to 30 weight %, based on the total weight of the cosmetic composition.

* * * * *

UNITED STATES PATENT AND TRADEMARK OFFICE
CERTIFICATE OF CORRECTION

PATENT NO. : 9,084,739 B2
APPLICATION NO. : 13/978625
DATED : July 21, 2015
INVENTOR(S) : Yong Chul Kim et al.

It is certified that error appears in the above-identified patent and that said Letters Patent is hereby corrected as shown below:

Title Page

Column 1, Item (73) Assignee, delete "Seonsan-si" and insert -- Seosan-si --

Column 2, OTHER PUBLICATIONS, Line 2, delete "methacryloyloxyethy1" and insert -- methacryloyloxyethyl --

Claims

Column 27, Lines 15-16, Claim 3, delete "(T-trimethylammonio" and insert -- (2'-trimethylammonio --

Signed and Sealed this
Sixteenth Day of February, 2016

Michelle K. Lee
*Director of the United States Patent and Trademark Office*